US009220856B2

(12) United States Patent
Martin et al.

(10) Patent No.: US 9,220,856 B2
(45) Date of Patent: Dec. 29, 2015

(54) METHOD AND APPARATUS FOR NON-INVASIVE MONITORING OF RESPIRATORY PARAMETERS IN SLEEP DISORDERED BREATHING

(75) Inventors: Dion Charles Chewe Martin, Concord (AU); John David Oates, Stanhope Gardens (AU)

(73) Assignee: RESMED LIMITED, Bella Vista (AU)

( * ) Notice: Subject to any disclaimer, the term of this patent is extended or adjusted under 35 U.S.C. 154(b) by 1126 days.

(21) Appl. No.: 11/664,685

(22) PCT Filed: Oct. 6, 2005

(86) PCT No.: PCT/AU2005/001543
§ 371 (c)(1),
(2), (4) Date: Apr. 5, 2007

(87) PCT Pub. No.: WO2006/037184
PCT Pub. Date: Apr. 13, 2006

(65) Prior Publication Data
US 2008/0066753 A1    Mar. 20, 2008

Related U.S. Application Data

(60) Provisional application No. 60/615,961, filed on Oct. 6, 2004, provisional application No. 60/629,612, filed on Nov. 22, 2004.

(51) Int. Cl.
*A61B 5/08*     (2006.01)
*A61M 16/00*    (2006.01)
(Continued)

(52) U.S. Cl.
CPC .......... *A61M 16/0051* (2013.01); *A61B 5/0826* (2013.01); *A61B 5/7278* (2013.01);
(Continued)

(58) Field of Classification Search
CPC .... A61B 5/0826; A61B 5/087; A61B 5/7282; A61M 16/0051; A61M 2016/0039; A61M 2230/04
USPC .............. 128/204.23, 204.21, 204.18, 205.23
See application file for complete search history.

(56) References Cited

U.S. PATENT DOCUMENTS 4,986,268 A * 1/1991 Tehrani .................... 128/204.22
5,388,575 A * 2/1995 Taube ...................... 128/204.23
(Continued)

FOREIGN PATENT DOCUMENTS

JP    11-318837       11/1999
JP    2001-321347     11/2001
(Continued)

OTHER PUBLICATIONS

D.J. Pitson, et al., Use of pulse transit time as a measure of inspiratory effort in patients with obstructive sleep apnoea, 8 Eur. Respir. J., 1669-1674 (1995).*
(Continued)

*Primary Examiner* — Lynne Anderson
*Assistant Examiner* — Peter S Vasat
(74) *Attorney, Agent, or Firm* — Nixon & Vanderhye, P.C.

(57) ABSTRACT

An air delivery system includes a controllable flow generator operable to generate a supply of pressurized breathable gas to be provided to a patient for treatment and a pulse oximeter configured to determine a measure of patient effort during a treatment period and provide a patient effort signal for input to control operation of the flow generator.

48 Claims, 10 Drawing Sheets

(51) Int. Cl.
*A61B 5/00* (2006.01)
*A61B 5/087* (2006.01)
*A61B 5/1455* (2006.01)

(52) U.S. Cl.
CPC .............. *A61B5/7282* (2013.01); *A61B 5/087* (2013.01); *A61B 5/1455* (2013.01); *A61M 2016/0039* (2013.01); *A61M 2230/04* (2013.01); *A61M 2230/205* (2013.01)

(56) References Cited

U.S. PATENT DOCUMENTS

| | | | |
|---|---|---|---|
| 5,662,106 A * | 9/1997 | Swedlow et al. | 600/331 |
| 5,682,877 A * | 11/1997 | Mondry | 128/204.23 |
| 5,704,345 A * | 1/1998 | Berthon-Jones | 128/204.23 |
| 5,954,050 A | 9/1999 | Christopher | |
| 6,091,973 A | 7/2000 | Colla et al. | |
| 6,325,761 B1 | 12/2001 | Jay | |
| 6,363,270 B1 | 3/2002 | Colla et al. | |
| 6,363,933 B1 * | 4/2002 | Berthon-Jones | 128/204.23 |
| 6,445,942 B1 | 9/2002 | Berthon-Jones | |
| 6,484,719 B1 * | 11/2002 | Berthon-Jones | 128/204.23 |
| 6,488,634 B1 * | 12/2002 | Rapoport et al. | 600/538 |
| 6,512,938 B2 * | 1/2003 | Claure et al. | 600/323 |
| 6,532,958 B1 * | 3/2003 | Buan et al. | 128/204.23 |
| 6,609,517 B1 * | 8/2003 | Estes et al. | 128/204.23 |
| 6,648,828 B2 * | 11/2003 | Friedman et al. | 600/506 |
| 6,675,797 B1 | 1/2004 | Berthon-Jones | |
| 6,702,752 B2 | 3/2004 | Dekker | |
| 6,796,305 B1 | 9/2004 | Banner et al. | |
| 7,425,201 B2 * | 9/2008 | Euliano et al. | 600/529 |
| 7,468,040 B2 | 12/2008 | Hartley et al. | |
| 2002/0165462 A1 * | 11/2002 | Westbrook et al. | 600/529 |
| 2003/0036689 A1 * | 2/2003 | Diab et al. | 600/323 |
| 2004/0040560 A1 * | 3/2004 | Euliano et al. | 128/204.23 |
| 2005/0061319 A1 | 3/2005 | Hartley et al. | |
| 2005/0217674 A1 * | 10/2005 | Burton et al. | 128/204.23 |
| 2007/0232951 A1 * | 10/2007 | Euliano et al. | 600/538 |

FOREIGN PATENT DOCUMENTS

| | | |
|---|---|---|
| JP | 2002-524177 | 8/2002 |
| JP | 2003-509134 | 3/2003 |
| JP | 2003-532445 | 11/2003 |
| JP | 2004-148069 | 5/2004 |
| JP | 2004-514116 | 5/2004 |
| JP | 2004-522483 | 7/2004 |
| JP | 2005-529713 | 10/2005 |
| JP | 2005-537068 | 12/2005 |
| JP | 5074191 | 11/2012 |
| WO | 00/45883 | 8/2000 |
| WO | 01/00264 | 1/2001 |
| WO | 01/19439 | 3/2001 |
| WO | 01/78601 | 10/2001 |
| WO | 02/28274 | 4/2002 |
| WO | 02/065901 | 8/2002 |
| WO | 03/000125 A1 | 1/2003 |
| WO | 2004/000114 | 12/2003 |
| WO | 2004/019766 | 3/2004 |
| WO | 2004/032719 | 4/2004 |
| WO | 2004/075746 A2 | 9/2004 |
| WO | 2006/037184 | 4/2006 |

OTHER PUBLICATIONS

Australian Patent Office Examiner's Report issued for Australian Patent Application No. 2005291858, dated Jul. 6, 2010.
Japanese Patent Office Examination Report issued for Japanese Patent Application No. 2007-534974, dated Jan. 4, 2011.
New Zealand Patent Office Examination Report issued for New Zealand Patent Application No. 554417, dated May 21, 2009.
International Search Report for PCT/AU2005/001543 mailed Dec. 7, 2005.
Hartert et al, "Use of Pulse Oximetry to Recognize Severity of Airflow Obstruction in Obstructive Airway Disease, Correlation with Pulsus Paradoxus", Chest 1999:115:475-481.
Kantelhardt et al., "Characterization of sleep stages by correlations in the magnitude and sign of heartbeat increments", Phys Rev E Stat Nonlin Soft Matter Phys., (2002).
Togo et al., "Decreased fractal component of human heart rate variability during non-REM sleep", Am J Physiol Heart Circ Physiol, 280: 17-21 (2001).
Dvir et al., "Evidence for fractal correlation properties in variations of peripheral arterial tone during REM sleep", Am J Physiol Heart Circ Physiol, 283: 434-439 (2002).
Chinese Office Action issued May 8, 2009 in Chinese Appln. No. 200580034088.8.
Australian Examiner's Report dated Dec. 1, 2011 for Patent Application No. 2011203234 (3 pages).
Office Action issued on Sep. 18, 2012 in corresponding Japanese Application No. 2011-081547 (with translation).
Japanese Office Action for Application No. 2012-275411, mailed Nov. 19, 2013 (w/English Translation) (2 pages).
Notification of the First Office Action in related Chinese Application No. 201310014931.2 with English translation, dated Sep. 28, 2014, 14 pages.
First Office Action in related Japanese Application No. 2013-158684 with English translation, dated Jun. 28, 2014, 8 pages.
Notification of the Fourth Office Action issued in related Chinese Application No. 201310014931.2, dated Jul. 13, 2015, (w/English translation), 11 pages.
Notification of the Second Office Action in related Chinese Application No. 201310014931.2 with English translation, dated Dec. 16, 2014, 14 pages.
Decision of Rejection issued in related Japanese Application No. 2013-158684, dated Mar. 2, 2015, (w/English translation), 6 pages.
Notification of Third Office Action issued in related Chinese Application No. 201310014931.2, dated Mar. 24, 2015, (w/English translation), 13 pages.
Second Office Action issued in related Japanese Application No. 2013-158684 dated Oct. 5, 2015, with English translation, 6 pages.

* cited by examiner

METHOD AND APPARATUS FOR NON-INVASIVE MONITORING OF RESPIRATORY PARAMETERS IN SLEEP DISORDERED BREATHING

CROSS REFERENCE TO RELATED APPLICATION

This application is the U.S. national phase of international application PCT/AU2005/001543 filed 6 Oct. 2005 which designated the U.S. and claims the benefit of U.S. Provisional Application No. 60/615,961 filed 6 Oct. 2004 and 60/629,612 filed 22 Nov. 2004, each incorporated herein by reference in its entirety.

FIELD OF THE INVENTION

The invention relates to monitoring of parameters relevant to Sleep Disordered Breathing (SDB).

BACKGROUND

Sleep Disordered Breathing (SDB) has been traditionally identified as being associated with Obstructive Sleep Apnea (OSA) and Cheyne-Stokes Respiration (CSR). Today there are a number of other conditions also recognised as being associated with SDB including, e.g., cardiovascular disease, stroke and diabetes, etc. Patients with these conditions and SDB may benefit from the treatment of their SDB with positive pressure ventilatory support by some form of mechanical ventilator.

While basic nasal Continuous Positive Airway Pressure (CPAP) ventilators may not monitor their patients, in general, the patients benefit from having a device which monitors the patients as part of some kind of control loop. In particular devices are known to monitor pressure, flow and patient effort.

An existing problem for known devices includes discriminating between obstructive sleep apnea (OSA) and central sleep apnea (CSA). OSA is indicative of upper airway collapse and can be used as an input to auto-titration algorithms for the CPAP pressure applied or the end-expiratory pressure (EEP) used in a bi-level device. CSA can be indicative of over-ventilation and can therefore be used as an input to algorithms that auto-titrate the ventilation of the patient. Clearly, miscategorising an apnea as either closed or open results in these titration algorithms prescribing sub-optimal parameters for the treatment of the patient.

Obstructive and central sleep apnea are discriminated in known devices by injecting a 1 cm peak-to-peak 4 Hz oscillation into the treatment pressure waveshape and measuring the resulting 4 Hz flow. The phasic difference in the flow to the pressure waveshape is indicative of the compliance of the load which is then used to deduce if the upper airway is opened or closed. However, this method is uncomfortable for the patient as 4 Hz is easily within the frequency band that can be perceived by the patient. Also, this method does not give any information on events that include upper airway narrowing/closure and simultaneous central sleep apnea.

Obstructive and central sleep apnea are also discriminated in known device by detecting the cardiogenic flow. The cardiogenic flow is the airflow induced in the lungs during a heart beat due to the proximity of the lungs to the heart. During OSA, there is therefore never any cardiogenic flow. Like the previous solution, it is also unable to determine if CSA and OSA have occurred concurrently.

Another existing problem for known devices includes inferring high patient respiratory effort. Patient respiratory effort is a key indicator used by clinicians when evaluating the acute state of a patient in a number of diseases including sleep apnea, obstructive lung disease, and various restrictive diseases. Despite its known value, it has not enjoyed widespread use as either an input to flow generator titration algorithms or as a recorded clinical parameter due to the inconvenience or impracticality of the transducers involved.

The "gold standard" in terms of accuracy for monitoring effort is an oesophageal catheter which a patient is required to swallow. Unfortunately, this is uncomfortable and awkward for a patient and not practical outside a clinic. Respiratory bands around the patient's chest and abdomen are known to monitor effort. Suprasternal notch effort sensors are also known, as well as the use of EMG and ECG sensors. These techniques are all unsuitable for home use.

Another existing problem for known devices includes measuring and storing vaso-specific parameters, such as cardiac afterload, vascular tone, heart rate variability, sympathetic nervous system activity in general, and/or central venous pressure. If these parameters were available in real-time in a flow generator, they could be used to (a) contribute to auto-titration algorithms and (b) be recorded with respiratory specific parameters to allow physicians to observe long-term trends and have a richer data set to determine the long term management of the patient.

Yet another existing problem for known devices includes limiting the mean mask pressure. Auto-titrating CPAP algorithms aimed at eliminating OSA or upper airway resistance syndrome (UARS) may use breath flow analysis to limit upper airway narrowing. Pressure beyond certain levels may, in some patients, be deleterious to cardiac function. Equally, a lower pressure may be beneficial to cardiac function provided it did not result in complete closure of the upper airway. It is desirable to include cardiovascular parameters in auto-titration schemes such that respiratory therapy (e.g., CPAP pressure) can be continuously optimised. Such parameters may include cardiac afterload, vascular tone, heart rate variability, sympathetic nervous system activity in general, and/or central venous pressure if they could be acquired non-invasively and conveniently.

ResMed's AutoSet CS and AutoSet CS2 devices specifically target patients with heart disease. These devices address the 'excessive CPAP pressure' problem by imposing a maximum average pressure of 15 cmH$_2$O.

Another known sensor is a suprasternal notch effort sensor. See U.S. Pat. No. 6,445,942 (Berthon-Jones). Other known techniques for monitoring apneas and hypopneas are described in U.S. Pat. No. 6,091,973 (Colla et al.) and U.S. Pat. No. 6,363,270 (Colla et al.). Another related U.S. patent is U.S. Pat. No. 5,704,345 (Berthon-Jones) which describes distinguishing open and closed airway apneas amongst other things. U.S. Pat. No. 6,484,719 (Berthon-Jones) describes a servo-ventilator which uses a flow sensor. The contents of all these patents are hereby expressly incorporated by cross-reference.

SUMMARY

In accordance with a first aspect of the invention, ventilator settings are adjusted in accordance with a parameter derived from pulse oximeter plethysmography. Ventilator settings that are adjusted include one of more of expiratory pressure, the level of support, rise-time and the ventilator wave-shape can be adjusted. Parameters derived from pulse oximeter plethysmography include one or more of pulse rate, effort, cardiac afterload, vascular tone, heart rate variability, sympathetic nervous system activity in general, and central venous pressure. In one form, ventilator mean treatment pressure is modulated in accordance with a parameter derived from pulse oximeter plethsmography. In another form, ventilator mean treatment pressure is decreased when pulse oximeter plethysmography indicates that a patient's vascular system is becoming stressed.

In accordance with a second aspect of the invention, pulse oximeter plethysmography is used to determine patient effort and the patient effort signal is used as an input to a feedback controller, the controller controlling positive pressure therapy delivered to the patient.

In accordance with a third aspect of the invention, pulse oximetry is used in conjunction with an airflow signal to distinguish open and closed airway apneas.

In accordance with a fourth aspect of the invention, a measure of patient effort is derived from a pulse oximeter plethysmograph signal, and the measure of effort is used as a control variable in a servo-ventilator. When the measure of patient effort increases, pressure support is reduced and when the measure of patient effort decreases, pressure support is increased.

Another aspect of the invention relates to a passive, non-invasive and convenient method of discriminating between obstructive and central sleep apnea, inferring high patient respiratory effort, measuring and storing vaso-specific parameters, and limiting mean mask pressure.

Yet another aspect of the invention relates to an air delivery system including a controllable flow generator operable to generate a supply of pressurized breathable gas to be provided to a patient for treatment and a pulse oximeter plethysmograph configured to determine a measure of patient effort during a treatment period and provide a patient effort signal for input to control operation of the flow generator.

Still another aspect of the invention relates to a method for treating sleep disordered breathing. The method includes providing a supply of pressurized breathable gas to a patient for treatment, using a pulse oximeter plethysmograph to determine a measure of patient effort during a treatment period and provide a patient effort signal, and controlling the supply of pressurized breathable gas based on input from the patient effort signal.

Parameters of interest (e.g., cardiac afterload, vascular tone, heart rate variability, and/or central venous pressure) can be estimated from a pulse oximeter plethysmograph. Currently, pulse oximeters are primarily employed for monitoring SpO2 and heart-rate. Some pulse oximeters display a plethysmograph, but as far as is known, none of the information present in the plethysmograph is used as input to auto-titrate respiratory or cardiovascular therapies. Peripheral Arterial Tone (PAT) is a novel multi-cell finger plethysmography system that focuses specifically on arterial tone. This technology may be an alternative to pulse oximetry as the sensing modality. Pulse-transit time (PTT) also contains information on autonomic activity and arterial tone.

Each aspect can be manifested in the form of a method and/or apparatus for non-invasive monitoring of one or more parameters relating to the diagnosis of a patient's health disorder, e.g., sleep disordered breathing, congestive heart failure, stroke, etc., and/or controlling a ventilator or other respiratory therapy device in accordance with the monitored parameter and/or the derived diagnosis.

Another aspect of the invention is to monitor a patient using pulse oximeter, plethysmography without treating them.

Further aspects of the invention are set out in the attached claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE FIGURES

The accompanying drawings facilitate an understanding of the various embodiments of this invention. In such drawings.

DETAILED DESCRIPTION OF ILLUSTRATED EMBODIMENTS

Figure 1:
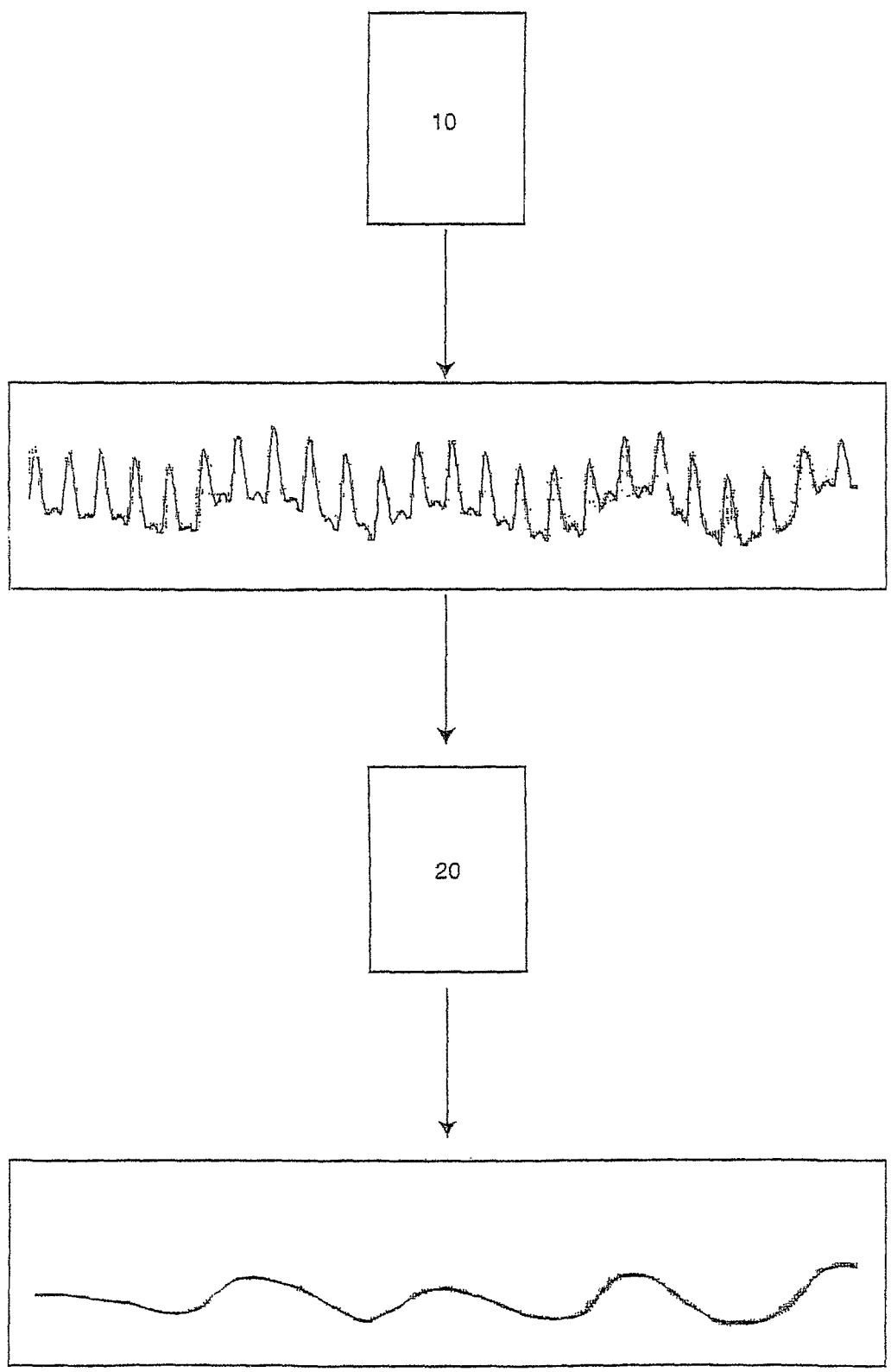
FIG. 1 shows a pulse oximeter waveform transformed into an effort signal.

Pulse oximeter plethysmography (sometimes referred to simply as "pulse oximetry" or "photo-plethysmogram") is a standard method of obtaining blood oxygenation data in a non-invasive and continuous manner. Oximeters use two wavelengths of light to solve for hemoglobin saturation. The waveforms are created by the absorption produced by pulsatile arterial blood volume, which represents the alternating current (AC) signal. The absorption produced by nonpulsatile blood, venous and capillary blood, and tissue absorption is depicted by the direct current (DC) signal. See Hartert et al, *Use of Pulse Oximetry to Recognize Severity of Airflow Obstruction in Obstructive Airway Disease, Correlation with Pulsus Paradoxus*, Chest 1999:115:475-481. A pulse oximeter signal from Hartert et al. is shown in FIG. 1.

Currently pulse oximeters are primarily employed for monitoring $SpO_2$ and heart-rate, however in accordance with an embodiment of the invention, the pulse oximeter is used as an indication of patient effort in a respiratory therapy device. Respiratory effort can be seen in the arterial blood pressure waveform as variation in the peak-to-peak amplitude. This is caused by the effect of the respiratory pleural pressure swings on cardiac output throughout the breathing cycle. Inspiration is associated with reduced systolic blood pressure, and this respiratory effect on blood pressure is referred to as 'pulsus paradoxus'.

This effect has been proposed as a measure of respiratory loading in various areas (asthma exacerbation, obstructive lung disease), where a variation of >10 mmHg is associated with high respiratory effort. The reference standard for measuring arterial blood pressure is invasive (catheter), so indirect methods are desired. One such method is pulse-transit time (PTT), where the variation in blood pressure causes a variation in vascular compliance, transduced as the propagation time of the pulse from the heart to the periphery. Another method is the oximeter plethysmographic waveform, which relates the volume of arterial blood in the tissue bed being sensed (usually finger or ear). Changes in cardiac output throughout the respiratory cycle may be seen as variation in the plethysmogram's peak-to-peak amplitude, consistent with the arterial blood pressure observations. This variation in cardiac output, combined with the variation in central venous pressure due to respiration, also induces changes in the baseline/offset of the PPG signal synchronous with breathing. A third factor seen in the PPG is affected by breathing: the heart period is also modulated somewhat by respiration, primarily via the respiratory neural outflow, and to a lesser extent in response to the arterial pressure variations induced by respiration.

Since the pulse oximeter plethysmogram is more related to volume of blood in the tissues, variation in the baseline/offset of the pulsatile component may be a more sensitive indicator of cardiopulmonary interaction than the cardiac output variation (Hartert et al.; Use of Pulse Oximetry to Recognize Severity of Airflow Obstruction in Obstructive Airway Disease—Correlation with Pulsus Paradoxis; Chest 1999; 115: 475-481).

Other factors (arterial tone, cardiac performance, postural changes) can also cause variations in the PPG, so processing is required to analyse the variation over the respiratory frequencies, and may be aided further by correlating the variation with respiratory flow information provided by the flow generator. A progressive increase in PPpleth (pulsus paradoxus from the plethysmogram) may indicate increasing efforts associated with impending upper airway (UA) collapse. A dramatic increase in PPpleth might indicate UA obstruction.

The waveform may be characterised into the following categories:

(a) Pulsatile amplitude: The AC amplitude of the pulse is most indicative of vascular compliance, which is greatly affected by arterial tone/sympathetic nervous system activity when looked at over 20-30 seconds or greater. As such, it can indicate arousal from apnea, and over many days/weeks, may demonstrate the long-term benefits of abolishing OSA/UARS on SNS activity. The finger is the best site for detecting the effect of autonomic activity on vascular compliance. Pulse oximetry at the ear is less sensitive to autonomic activity, but may offer an estimation of relative blood pressure variation, given that vascular compliance exerts a lesser effect.

(b) Offset or baseline: Respiration induces a phasic variation in the pulse baseline (pulsus paradoxus) that varies in accordance with respiratory effort (the pressor response). This effect has been used to identify airway resistance (asthma) and obstruction (obstructive lung disease). See Comparison of traditional and plethysmographic methods for measuring pulsus paradoxus (Clark J et al. Arch Pediatr Adolesc Med 2004. 158: 48-51) and use of pulse oximetry to recognize severity of airflow obstruction in obstructive airway disease; correlation with pulsus paradoxus (Hartert et al. Chest 1999. 115: 475-481. Available online at http://www.chestjournal.org/cgi/reprint/115/2/475).

(c) Pulse rhythm: Irregular heart rhythm can be detected, particularly (but not exclusively) when combined with ECG activity. A beat-to-beat shifting of pulse amplitude after a pause can indicate irregular rhythm. Availability of ECG allows pulse-transit time to be calculated, another indicator of vascular tone, which may augment the sensitivity or specificity of any conclusions regarding arousal, respiratory effort, or sympathetic tone. Heart-rate variability indices can be calculated from the pulse period, inferring sympatho-vagal balance. Fractal components in the HRV data can distinguish sleep-wake state.

(d) Waveshape: The wave morphology contains similar information to that seen in arterial catheter pressure signals or applanation tonometry. For example, the position and relative amplitude of the dicrotich notch can point to the degree and timing of pressure-wave reflections from the peripheral circulation, itself an indicator of vasomotor tone (SNS). Venous pulsation may also be apparent in the waveform, which represents interaction between a number of factors, but in our case may indicate the effect of excessive CPAP (increased central venous pressure) or improvement in congestive heart failure (reduced central venous pressure). The first-derivative of the plethysmogram is closely related to arterial flow to the area, while the second-derivative of the waveform has been proposed as an indicator of vasoactivity and arterial compliance.

Methods for extracting the above parameters from the raw PPG exist, for example, time-domain or frequency-domain signal processing techniques, or elements of both. One example are the methods taught in WO 03/00125 A1 and WO 2004/075746 A2, employing the continuous wavelet transform to extract the respiratory signals and arterial tone information from the raw PPG. Time-domain analysis of assessing baseline fluctuations from the PPG are summarised by Shamir et al, British Journal of Anaesthesia 1999, 82(2): 178-81.

Recent developments in oximeter signal processing has allowed device performance to be more robust when presented with movement and low perfusion. Modern embedded processors allow more sophisticated post-processing of plethysmographic waveforms, and even the most advanced oximeter technology is available as OEM module format. These technological advances, together with the underlying information present in the plethysmogram combined with information from the therapy device, may permit a respiratory device to employ an oximeter as part of a servo-controlled therapy.

The information present in the plethysmogram may be useful to diagnosis-only studies as well, since it can indicate arousals that may not be evident as a desaturation.

Respiratory effects can also be seen as variation in cardiac timing, termed 'respiratory sinus arrythmia', which may also be used to extract respiratory timing information.

An aspect of the invention relates to the combination of (1) oximeter plethysmograph-derived parameters with (2) respiratory flow information, to augment real-time control algorithms for a respiratory therapy device.

This arrangement may prove superior to current techniques if it permits a more thorough and timely estimate of the patient's acute condition allowing algorithms to prescribe more appropriate therapy. The parameters are also optionally stored within the flow generator to give a physician a richer data set for long term patient management. This is superior to current technologies as it gives a physician data from flow generators used in an unsupervised environment similar to that gained in a sleep study.

Plethysmographic parameters useful for titration and long term patient management include all those noted above (patient effort, vascular compliance, heart rate variability, arrhythmia detection, venous pulsation, and SpO2).

In accordance with an embodiment of the invention, a pulse oximeter signal 10 is fed through signal processor 20, for example, a low pass filter, peak detection, nadir detection or averaging. The filter is designed to remove signals indicative of heart rate and leave signals indicative of respiratory rate.

Figure 2:
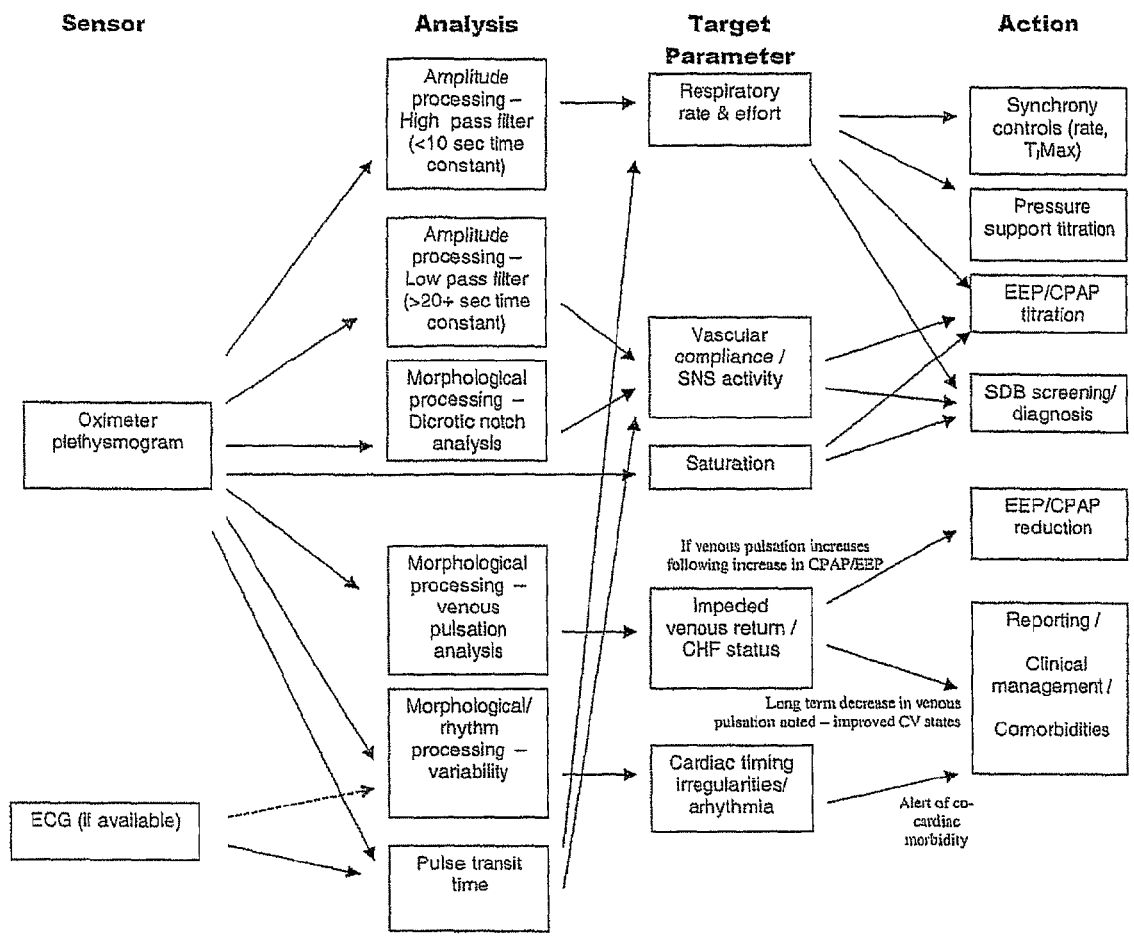
FIG. 2 shows a range of pulse oximetry applications in accordance with various embodiments of the invention.

Once the effort signal is derived from the pulse oximeter, it may be used in a number of ways as shown in FIG. 2 and described in further detail below:

(i) Open-Closed Apnea Discrimination. The plethysmographically derived respiratory effort estimate can be used during episodes of apnea (using respiratory flow data) to indicate whether the apnea is opened (non-obstructed) or closed (obstructed), useful in automatic titration algorithm logic. For example, a low or zero flow signal is indicative of an apnea. If the apnea occurs in the absence of effort as measured by the pulse oximeter, then the apnea is regarded as being, "open". However, if there is effort, then the apnea is regarded as being "closed".

(ii) High airway resistance. Similarly, a period of high respiratory effort derived from the oximeter plethysmograph combined with reduced respiratory flow or with flow limitation (inferred by flow waveshape) can imply the presence of significant airway resistance, be it due to expiratory flow limitation or upper-airway resistance. In both cases, the combination of high effort and low measured respiratory flow may be an indicator to increase applied PEEP.

(iii) Relative work of breathing: In the absence of respiratory flow limitation (adjudged from respiratory flow waveshape or estimated volumes), persistently high respiratory effort may indicate inadequate pressure support (under-ventilation).

(iv) Used in conjunction with a flow based measure of phase (such as described in U.S. Pat. No. 6,484,719).

(v) Using the effort waveshape to augment ResMed's AutoSet CPAP algorithm. Increasing patient effort is indicative of impending upper-airway instability. AutoCPAP titration based on increased patient effort may be more pre-emptive of obstruction than the current flattening based algorithm.

(vi) Using the effort information as a basis for an algorithm in a ResMed's VPAP or AutoCS device to titrate applied PEEP. It is conceivable that titration algorithms based on inspiratory waveshape will be challenged when used in devices that change the pressure during the breath cycle. Changes in patient effort are not as dependent on intra-breath changes in pressure and hence should be more robust to these types of therapy.

(vii) Using the effort waveshape as an early indicator that a patient has been overventilated. This may be a possible consequence of inappropriate servo-ventilation, where a ventilator augments the patient's ventilation to achieve a target level. This indicator can be used to titrate the target ventilation.

(viii) Using venous pulsation as an input to ResMed's AUTOSET CPAP algorithms for patients with OSA and heart failure. Increases in venous pulsation can be used to limit the CPAP pressure applied to safer limits.

(ix) Using vascular compliance as an input to ResMed's CPAP algorithms. Changes in vascular compliance can be indicative of patient arousals. This can be used to augment the data currently used for automatically prescribing CPAP levels.

(x) Comparison of the respiratory effort estimate with the respiratory device's own estimate of breath phase (parameter used in ResMed's AutoCS2 and AutoVPAP) may allow a more robust breath-tracking scheme within the respiratory device; for example, it may improve leak rejection or leak estimation.

(xi) Sleep state—detection of non-REM sleep. REM sleep is similar to wake periods in the fractal component of HRV (see http://www.ncbi.nlm.nih.gov/entrez/query.fcgi?cmd=Retrieve&db=pubmed&dopt=Abstract&list_uids=12059594; http://ajpheart.physiology.org/cgi/reprint/280/1/H17; http://ajpheart.physiology.org/cgi/reprint/283/1/H434), but the non-REM sleep stages differ significantly from awake. HRV data might be analysed to indicate sleep onset, since the patient must pass through non-REM sleep prior to achieving REM sleep. The PPG inherently monitors heart period, and provided this period information is not averaged, can be used to conduct traditional HRV analyses. One method of discriminating sleep/wake from HRV is taught by Ivanov et al, Europhysics Letters 1999, 48(5): 594-6000.

Analysis of the plethysmographic waveshape, possibly in combination with other monitored variables, may be used to optimise CPAP or VPAP therapies to reduce arterial stiffness, independently associated with poor cardiovascular prognosis. For example:

(i) By combining the timing of the cardiogenic respiratory flow signal with the timing of the plethysmographic pulse it may be possible to calculate relative variations in pulse-transit time more accurately than traditional PTT (pulse transmission time) estimates. Traditional methods that employ the ECG for cardiac timing information include both the pre-ejection period and the pulse transit time. By contrast, cardiogenic flow is induced by the actual ventricular ejection. Accurate PTT estimation may offer additional information to that of the plethysmograph alone, contributing to the estimation of arterial tone/SNS activity and/or respiratory effort, and allowing closed-loop therapies aiming to optimise arterial compliance.

(ii) The morphology of the plethysmographic waveform may offer information directly associated with vascular compliance, for example, the position of the so-called 'diochrotic notch' relative to the initial systolic peak, allowing closed-loop therapies aiming to optimise arterial compliance.

With reference to FIG. 3-7 it is noted that:
THERAPY ALGORITHM adjustments may include:
Level of PEEP/CPAP
Level of Pressure support
Concerning the two feedback signals F/B1 and F/B2 it is noted that:
F/B 1 (Airflow-inferred patient parameter) may include any or all of the following:
Minute ventilation estimate
Inspiratory airflow limitation (e.g., UA flattening index)
Expiratory airflow limitation (e.g., expiratory flow waveform morphology)
Tidal volume
Leak
Cardiac timing (time of systolic ejection, extracted from cardiogenic flow)
Respiratory phase
F/B 2 (PPG-inferred patient parameter) may include any or all of the following:
Relative indication of respiratory effort (e.g., high effort leads to increased respiratory baseline variation of PPG, pulsus paradoxus)

Absolute indication of respiratory rate

Patterns of respiratory effort and rate indicative of respiratory control anomalies or apnea type (crescendo/decrescendo in breathing effort, statistical derivations from respiratory patterns)

Indication of respiratory rate (e.g., variation of PPG amplitude and timing parameters)

Relative indication of worsening cardiac function (e.g., cardiac decompensation results in increased respiratory baseline variation of PPG, pulsus paradoxus)

Relative indication of venous congestion (e.g., degree of venous pulsation in PPG—morphological analysis)

Relative variation in sympathetic nervous system activity or arterial compliance (e.g., variation of PPG pulse amplitude over >20-30 second timescale, or shift in location of dicrotic notch)

Standard pulse oximetry ($SpO_2$)

Arrival time of systolic pulse at periphery (e.g., systolic rise in PPG).

Pulse rate

CLINICAL TARGETS may include:

Minimum ventilation (e.g., Respiratory Insufficiency, Obesity Hypoventilation patients)

Nominal ventilation (e.g., Cheyne-Stokes Respiration patients)

Optimal synchrony

Sleep quality (all patients)

Long-term cardiac function (e.g., CHF/CSR/hypertensive patients).

Anticipation/prediction of cardiac decompensation (e.g., CHF patients)

Optimal arterial compliance

Minimum CPAP/EEP/PEEP

Maximum CPAP/EEP/PEEP

Minimum Pressure Support

Maximum Pressure

Maximum Average Pressure

Figure 3:
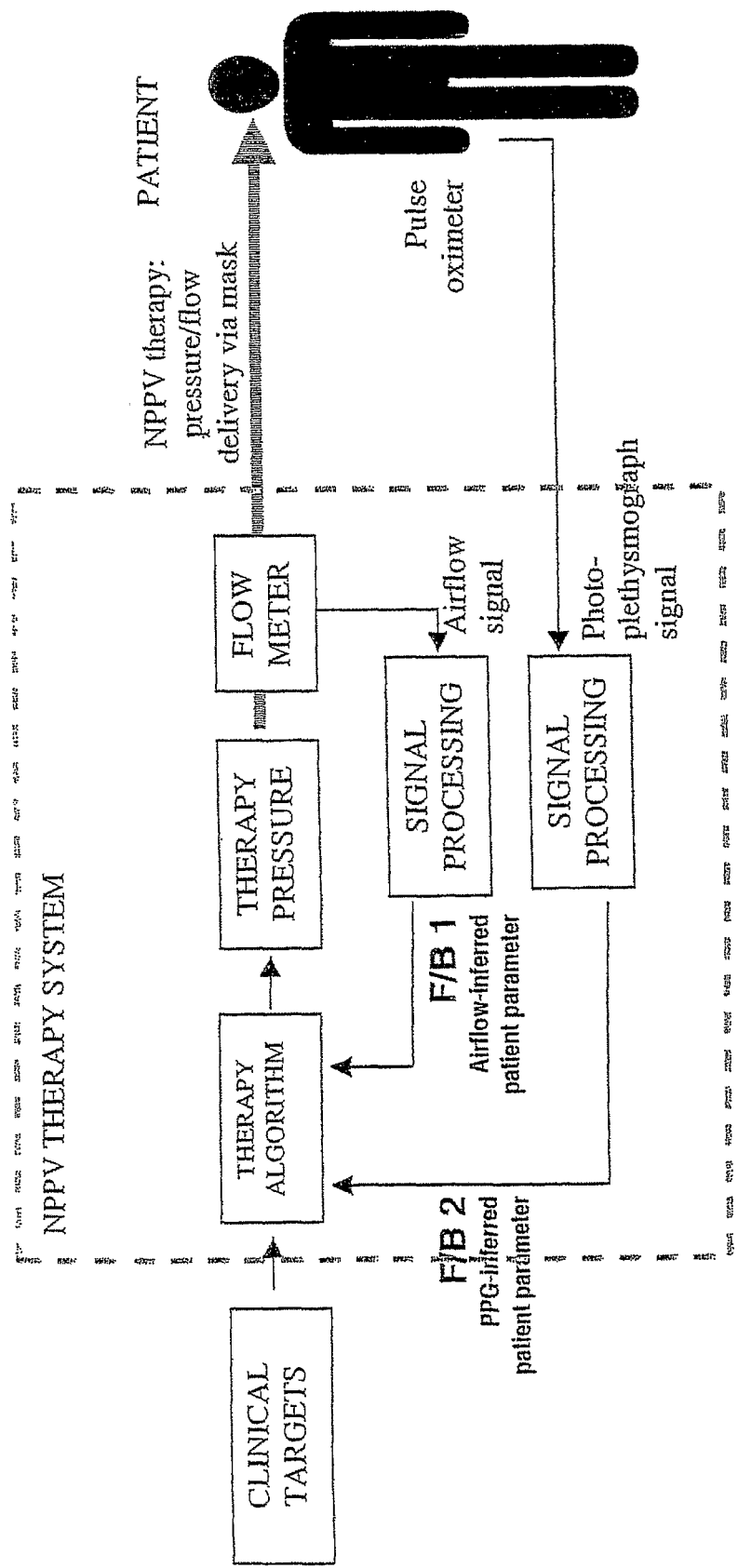
FIG. 3 shows a therapy system in accordance with an embodiment of the invention.
Figure 3A:
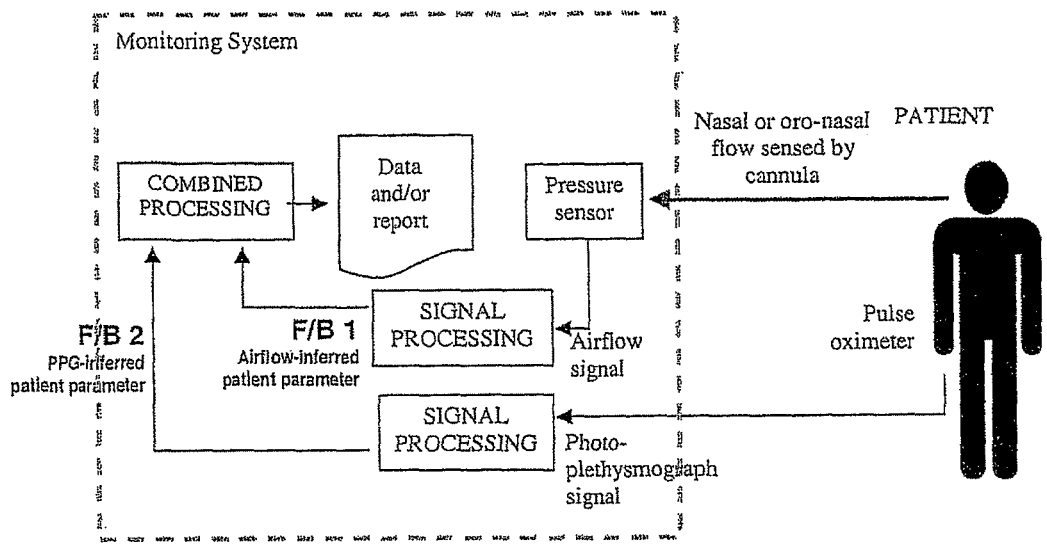
FIG. 3A is a schematic diagram of a monitoring system according to an embodiment of the present invention.

FIG. 3A is a schematic diagram for a monitoring system according to an embodiment of the present invention. Concerning the feedback signals F/B1 and F/B2, and the "Combined Processing" box, it is noted that:

F/B 1 (Airflow-inferred patient parameter) may include any or all of the following:

Inspiratory airflow limitation (e.g., UA flattening index)

Expiratory airflow limitation (e.g., expiratory flow waveform morphology)

Cardiac timing (time of systolic ejection, extracted from cardiogenic flow)

Respiratory phase

Time course of breath amplitude and derived statistics

F/B 2 (PPG-inferred patient parameter) may include any or all of the following:

Relative indication of respiratory effort (e.g., high effort leads to increased respiratory baseline variation of PPG, pulsus paradoxus)

Absolute indication of respiratory rate.

Relative indication of worsening cardiac function (e.g., cardiac decompensation results in increased respiratory baseline variation of PPG, pulsus paradoxus)

Relative indication of venous congestion (e.g., degree of venous pulsation in PPG—morphological analysis)

Relative variation in sympathetic nervous system activity or arterial compliance (e.g., variation of PPG pulse amplitude over >20-30 second timescale, or shift in location of dicrotic notch)

Standard pulse oximetry ($SpO_2$)

Arrival time of systolic pulse at periphery (e.g., systolic rise in PPG).

Pulse rate

COMBINED PROCESSING may include:

Delay between respiration changes (F/B 1) and blood gas adjustments (F/B 2), eg to infer circulatory delay.

Pulse transit time (PTT) indicated by delay between cardiogenic flow pulses (F/B 1) and arrival of the pulse at the periphery (F/B 2).

CLINICAL MONITORING TARGETS may include:

Assessment of SDB

Assessment of sleep quality (all patients)

Assessment of cardiac function (e.g., CHF/CSR/hypertensive patients) as an adjunct to patient management.

FIGS. 4-7 show a number of algorithms performing various embodiments of the invention. Embodiments of the invention may take the form of a method and/or apparatus to monitor, in a non-invasive manner, one or more parameters, e.g., pulse oximetry and/or air flow, relating, e.g., to a patient's breathing and/or heart activity.

The monitored parameter or parameters may be used for diagnostic purposes, e.g., to log data, to produce a report or an alarm or otherwise signal a physician. In addition, or in the alternative, the values of the monitored parameter(s) may be used to control, e.g., stop, start or vary, the delivery of pressurized gas (e.g., timing, flow pressure) from a blower, ventilator or the like, to the patient.

Figure 4:
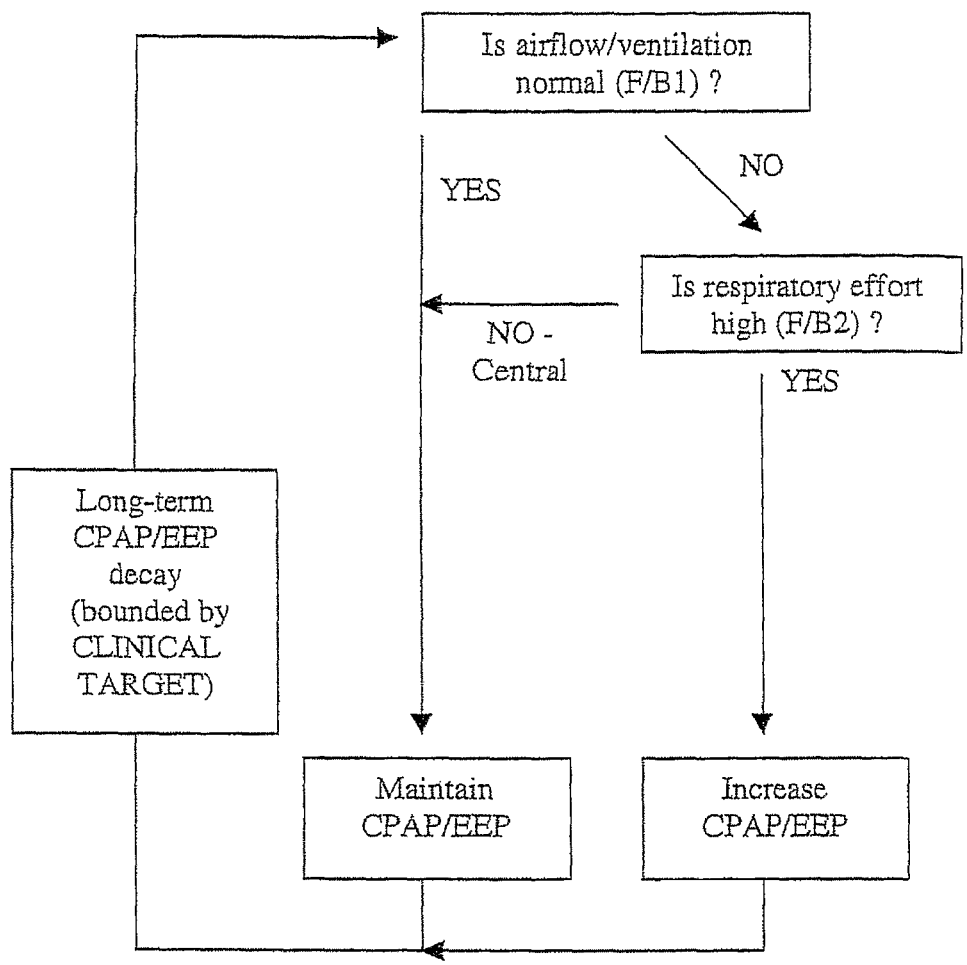
FIG. 4 shows an algorithm for Upper-airway obstruction (inspiratory flow limitation) and Auto-EEP/AutoCPAP in accordance with an embodiment of the invention.

FIG. 4 shows an open/closed airway apnea algorithm. An airflow signal is analysed and a determination is made as to whether it is within normal bounds. If it is then CPAP/EPAP therapy is maintained at its current level. If the airflow signal is not normal, for example low indicative of an apnea, then the effort signal is analysed. If the effort is high then an obstructive apnea may be indicated and the appropriate therapy is to increase the treatment pressure.

Figure 5:
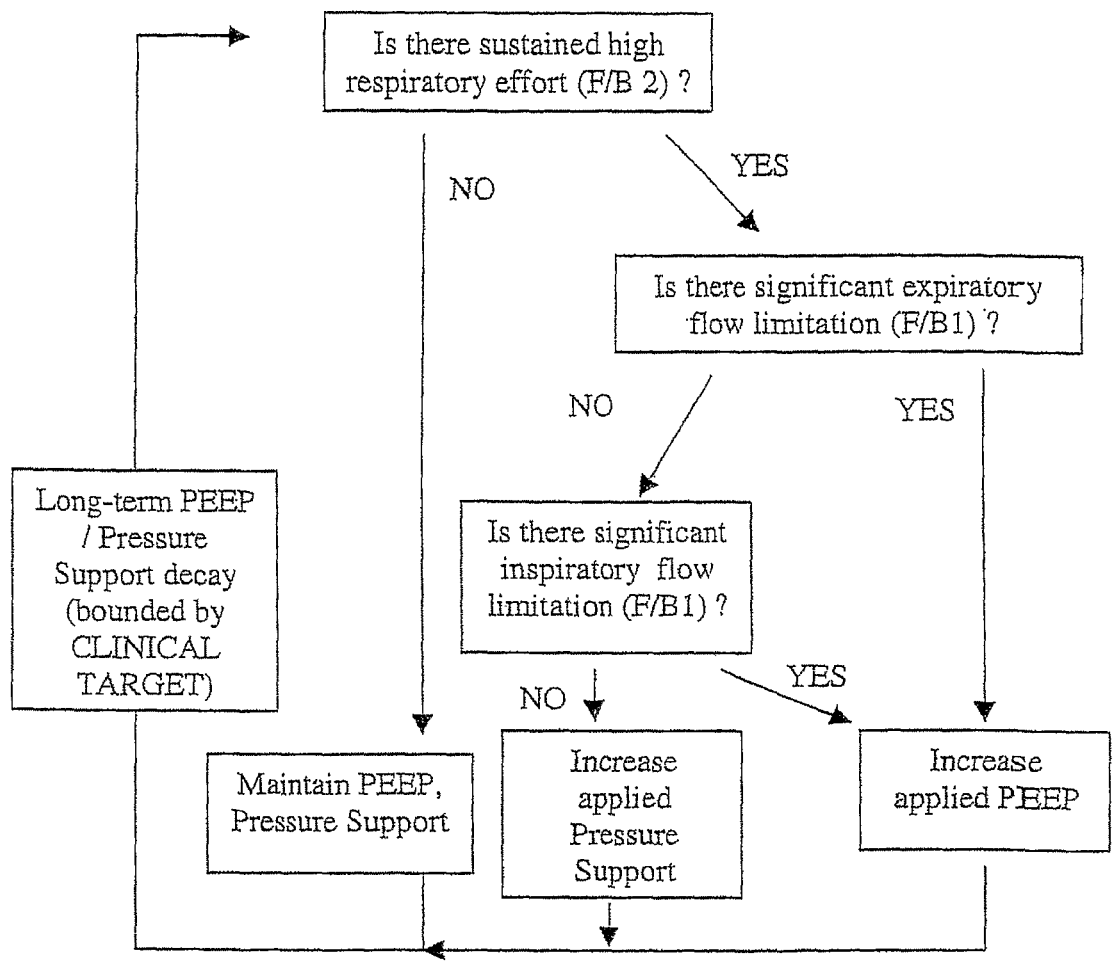
FIG. 5 shows an algorithm for Auto-EEP titration/Automated Pressure Support titration in accordance with an embodiment of the invention.

FIG. 5 shows an algorithm for patients suffering general respiratory insufficiency. The algorithm defines when pressure support, or End Expiratory Pressure (EEP) should be varied.

Figure 6:
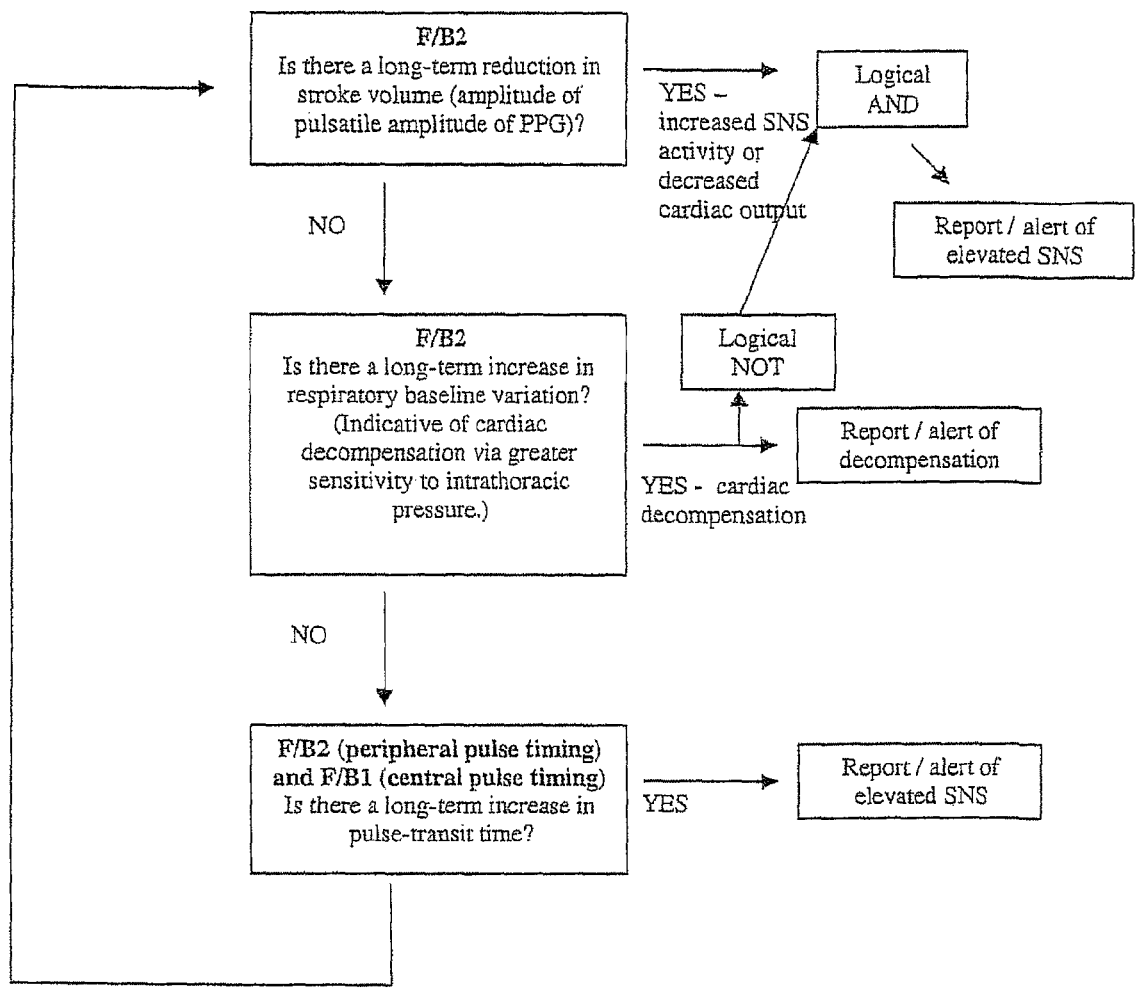
FIG. 6 shows an algorithm for Detection of elevated Sympathetic Nervous System (SNS) or reduced cardiac output—cardiac patients on CPAP/AutoCPAP/Comfort (fixed low-support bilevel) devices in accordance with an embodiment of the invention.

FIG. 6 shows an algorithm which may be part of a monitoring system for evaluating cardiac performance. A cardiac patient may be receiving CPAP therapy and have an additional monitoring device with the algorithm of FIG. 6. Alternatively the CPAP device may incorporate the pulse oximeter. The two signals F/B/1 and F/B/2 are analysed. Where the values are indicative of elevated levels of SNS activity, or decompensation (poor cardiac performance) an alert is generated. The alert may be in the form of an audible alarm, or part of a messaging system which reports to a physician.

Figure 7:
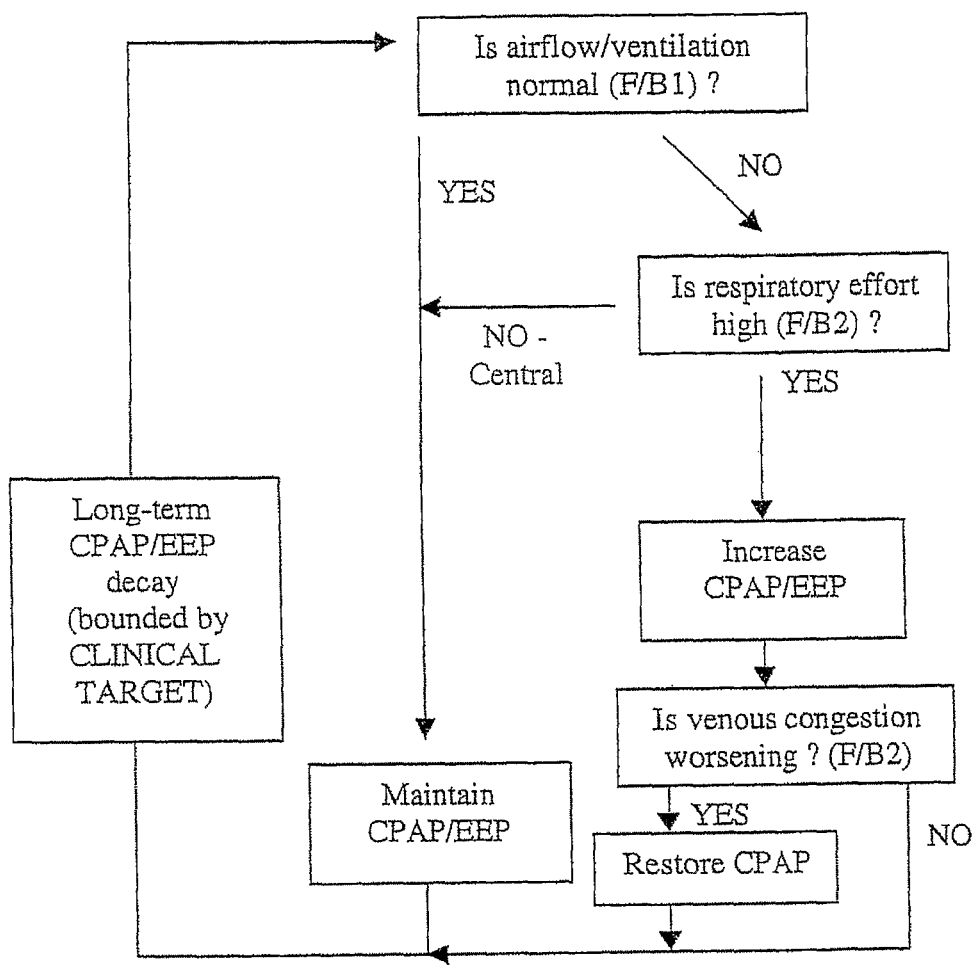
FIG. 7 shows an algorithm for AutoCPAP on cardiac patients in accordance with an embodiment of the invention.

FIG. 7 depicts an algorithm for cardiac patients on CPAP therapy. The algorithm is similar to that in FIG. 4. However, it has the additional step that venous congestion is monitored through the pulse oximeter. If venous congestion is worsening, then CPAP pressure will not be increased, but restored to a previous level.

Figure 8:
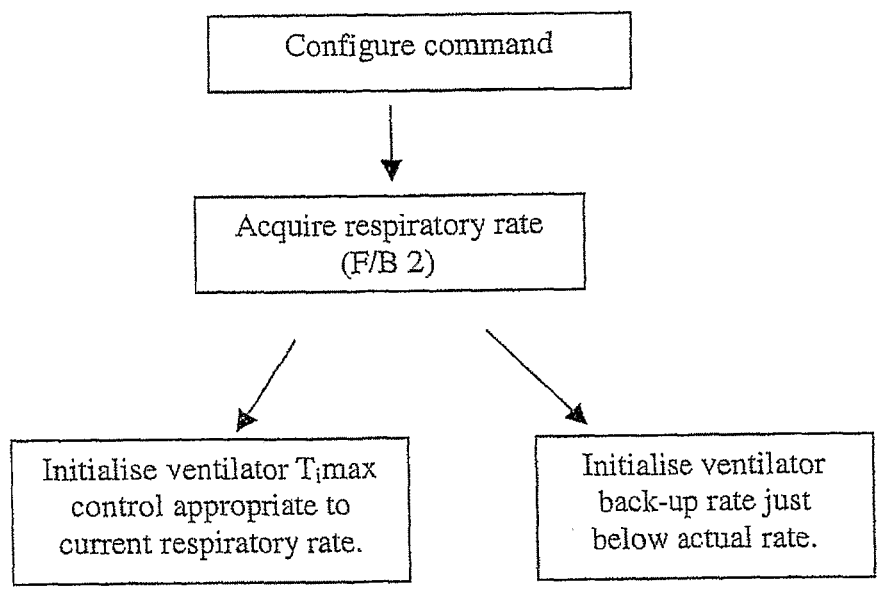
FIG. 8 is a block diagram illustrating a procedure for initializing NPPV therapy rate settings, based on respiratory rate information, in accordance with an embodiment of the present invention.

FIG. 8 depicts a procedure for initializing NPPV therapy rate settings, based on respiratory rate information. Preferably, this is performed after attaching oximeter probe (F/B2), but can be attached prior to commencing ventilation.

Figure 9:
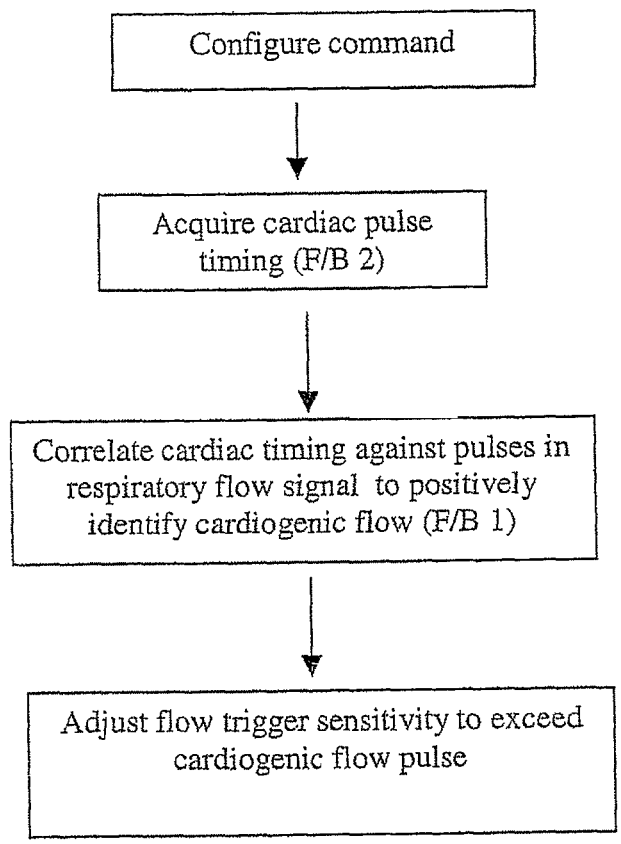
FIG. 9 is a block diagram illustrating a procedure for initializing NPPV therapy trigger threshold settings, based on positively identifying cardiogenic flow amplitude, in accordance with an embodiment of the present invention.

FIG. 9 depicts a procedure for initializing NPPV therapy trigger threshold settings, based on positively identifying cardiogenic flow amplitude. Preferably, this is performed once ventilation is initiated, e.g., so a respiratory flow signal is available.

The combination of traditional oximetry data (saturation, heart rate, pulse timing information) and respiratory timing and effort information (inferred from additional processing of a PPG and/or from the addition of a nasal or oronasal cannulae data) may permit new diagnostic possibilities. For example:

Circulatory delay (delay between breathing changes and saturation changes), possibly an indicator of heart-failure severity or cardiac decompensation.

'True' Pulse Transit Time (PTT), via the delay between cardiogenic flow pulses seen by the nasal pressure transducer at end-expiration (seen at the nares) and the arrival of pulse at the periphery (from the oximeter plethysmogram). PTT measurement is an indicator of arousal (transient increases in sympathetic outflow and BP) and possibly an indicator of average BP/average sympathetic activation when viewed over longer periods. Traditionally, PTT is calculated based on the ECG for central cardiac timing (systole) and the PPG for peripheral pulse timing. Using cardiogenic flow for central cardiac timing may have advantage over ECG-derived PTT in that the cardiogenic flow (CGF) represents mechanical ejection (with a fixed propagation delay from lung to nares) rather than electrical activation of the left-ventricle, so removes the pre-ejection period from the measurement. The pre-ejection period is known to sometimes detract from the sensitivity of the ECG-derived PTT measurement. By acquiring the CGF at a consistent portion of the respiratory cycle (end expiration, when it is most readily seen), the respiratory-induced fluctuations in PTT may be ignored. That leaves just the PTT variations due to either BP variation or increased arterial tone (sympathetic activation), both of which shorten the PTT, and both of which are associated with arousal, thereby offering another important SBD parameter.

By extracting respiratory effort information from the raw PPG (pulsus paradoxus) a simple diagnostic system may offer all the key information required for SBD screening except sleep staging: breathing pattern, oxygen saturation, arousal (PTT) or increased SVR, and high effort periods (apnea discrimination and RERA classification). This system may or may not include a nasal pressure transducer, depending on the relative importance of the derived signals. Nasal airflow combined with respiratory effort permits straightforward discrimination between central and obstructive apneas, but signal processing may glean the same information from combining information from the PPG, e.g., time course of breathing effort compared to time course of desaturations, or statistical analysis of the time course of breathing effort.

Other specific examples of where aspects of the invention may be used include:

(a) Using respiratory-related cardiac variations (e.g., "respiratory sinus arrhythmia") to track and predict breath-phase, and to use the prediction for ventilator triggering. Such variations may conveniently be detected in the PPG, but may also be detected by other cardiac monitoring devices such as ECG electrodes. Typically the respiratory variation imposed on cardiac performance occurs too late to be used as a ventilator trigger; ventilators ideally offer respiratory support coincident with early inspiration, preferably within 100 msec of the patient's initial inspiratory effort. Ventilators typically monitor inspiratory flow or airway pressure variations as a trigger. In severe obstructive respiratory disorders (e.g., COPD) the respiratory flow or pressure information is a poor indicator of inspiratory timing. In such disorders, an alternative 'window' into respiratory activity may offer superior results. Respiration, particularly laboured respiration, is known to affect cardiac timing and cardiac output. By monitoring cardiac performance over previous breath cycles, and deriving a respiratory phase signal from cardiac information, it is proposed that the timing of the next inspiratory effort may be predicted, provided the latency of extracting the respiratory signal is not excessive (e.g., more than 1 breath delayed). The central-to-peripheral propagation time for the pulse is typically around 200 msec (the "pulse transit time"), and at best the cardiac cycle would offer a low sample-rate estimate of breath phase (about 4-6 beats per breath). So it is unlikely that a prediction of breath phase could occur sooner than 0.5 breaths in advance, and thus may not offer precise inspiratory timing. However, such a method may still offer significant utility in disease states such as COPD, where ventilator synchronisation via respiratory flow is traditional very delayed, and where breath timing may be more entrained than in normal breathing (and therefore predictability being potentially greater).

(b) Using HRV analysis to infer sleep onset within a screener device, or sleep structure within a therapy device.

(c) In a ventilator system equipped with customised PPG monitoring, detecting dramatic drop in cardiac output (inferred from PPG amplitude reductions), and asserting an alarm. A drop in cardiac output may be a consequence of many clinically relevant circumstances, e.g., applying excessive positive pressure in a patient with hypovolemia (Yamakage, Can J Anesth 2005 52(2): 207), excessive dynamic hyperinflation/air trapping (Perel, B J A 76(1):168-169) (Conacher, Lancet 1995 346:448).

Advantages for the patient include, for example, more comfort and ease of use. Aspects of the invention provide optimal therapy without being festooned with sensors, e.g., a finger or ear probe is sufficient. Advantages for the physician include, for example, ease to administer. Aspects of the invention provide simple application, automated therapies, and long term patient management feedback. Other advantages include less expensive and improved therapy.

Although the invention has been described with reference to particular embodiments, it is to be understood that these embodiments are merely illustrative of the application of the principles of the invention. Numerous modifications may be made therein and other arrangements may be devised without departing from the spirit and scope of the invention. For example, those skilled in the art recognise that there are other indications of upper airway instability, resistance or obstruction which are not necessarily accompanied by or associated with flow flattening.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. A method for delivering positive pressure therapy by a CPAP ventilator to a patient having a health disorder, the method comprising:

receiving a pulse oximetry signal from a pulse oximeter;

forming a patient respiratory effort signal from the pulse oximetry signal with a processor;

analyzing the patient respiratory effort signal with the processor to arrive at an indication of patient respiratory effort associated with inspiring air into the lungs;

measuring patient respiratory airflow and generating a patient respiratory airflow signal with a pressure sensor or a flow meter; and controlling positive pressure therapy delivered to the patient by the ventilator by inputting the patient respiratory effort signal and the patient respiratory airflow signal to a feedback controller of the ventilator.

2. The method of claim 1, wherein the health disorder is sleep disordered breathing, congestive heart failure, or stroke.

3. The method of claim 1, further comprising processing the pulse oximeter signal with a signal processor to remove signals indicative of heart rate and leave signals indicative of respiratory rate.

4. The method of claim 3, wherein the signal processor further comprises a low pass filter, peak detector, nadir detector or averaging.

5. The method of claim 1, wherein when an absence of respiratory flow limitation is detected based on the patient respiratory airflow signal, persistently high patient respiratory effort indicates inadequate pressure support.

6. The method of claim 1, further comprising titrating applied PEEP based on the patient respiratory effort signal.

7. The method of claim 1, wherein a waveshape of the patient respiratory effort signal indicates that the patient has been overventilated.

8. The method of claim 7, further comprising titrating a target ventilation based on the waveshape of the patient respiratory effort signal.

9. The method of claim 1, further comprising determining a measure of venous pulsation from the patient respiratory effort signal with the processor; and
using the measure of venous pulsation as an input to a CPAP algorithm for patients with OSA and heart failure.

10. The method of claim 9, further comprising limiting the CPAP pressure applied by the CPAP ventilator in response to increases in the measure of venous pulsation.

11. The method of claim 1, further comprising determining a measure of vascular compliance from the patient respiratory effort signal with the processor; and
using the measure of vascular compliance as an input to a CPAP algorithm.

12. The method of claim 11, wherein changes in the measure of vascular compliance are indicative of patient arousals.

13. The method of claim 12, further comprising augmenting data for prescribing CPAP levels with the measure of vascular compliance.

14. The method of claim 1, further comprising adjusting amplitudes of the pulse oximetry signal with a high pass filter in connection with a predetermined time constant.

15. The method of claim 14, further comprising providing patient respiratory effort information with the feedback controller to synchrony controls, pressure support titration, EEP/CPAP titration, and/or SDB screening/diagnosis functions of the CPAP ventilator.

16. The method of claim 1, wherein a baseline signal of the pulse oximeter is the only signal used in forming the patient respiratory effort signal that is inputted to the feedback controller.

17. The method of claim 1, further comprising:
determining whether an apnea has occurred based on the patient respiratory airflow signal; and
if an apnea is detected, determining whether the apnea is open or closed based on the patient respiratory effort signal.

18. The method of claim 1, further comprising determining that airway resistance is occurring when a decrease in the patient respiratory airflow signal and an increase in the patient respiratory effort signal are detected.

19. The method of claim 18, wherein airway resistance further comprises expiratory flow limitation or upper-airway resistance.

20. The method of claim 19, further comprising increasing applied PEEP when the decrease in the patient respiratory airflow signal and the increase in the patient respiratory effort signal are detected.

21. The method of claim 1, further comprising determining that upper-airway instability is impending when an increase in the patient respiratory effort signal is detected.

22. The method of claim 1, wherein if the patient respiratory airflow signal is normal, then CPAP/EEP therapy is maintained, and
wherein if the patient respiratory airflow signal is not normal, then the patient respiratory effort signal is analyzed,
wherein if the patient respiratory airflow signal is not normal and the patient respiratory effort signal is high, then CPAP/EEP therapy is increased, and
wherein if the patient respiratory airflow signal is not normal and the patient respiratory effort signal is not high, then CPAP/EEP therapy is maintained.

23. The method of claim 22, wherein:
if CPAP/EEP therapy is increased, then the method further comprises determining venous congestion based on the pulse oximetry signal, and
if venous congestion is determined to be worsening, then CPAP therapy is restored.

24. The method of claim 1, further comprising:
measuring inspiratory flow and generating an inspiratory flow limitation signal with the processor; and
measuring expiratory flow and generating an expiratory flow limitation signal with the processor,
wherein:
if the patient respiratory effort signal is not high, then PEEP and pressure support are maintained,
if the patient respiratory effort signal is high, the expiratory flow limitation signal is not indicative of significant expiratory flow limitation, and the inspiratory flow limitation signal is not indicative of significant inspiratory flow limitation, then applied pressure support is increased,
if the patient respiratory effort signal is high, the expiratory flow limitation signal is not indicative of significant expiratory flow limitation, and the inspiratory flow limitation signal is indicative of significant inspiratory flow limitation, then applied PEEP is increased, and
if the patient respiratory effort signal is high and the expiratory flow limitation signal is indicative of significant expiratory flow limitation, then applied PEEP is increased.

25. An air delivery system, comprising:
a controllable flow generator operable to generate a supply of pressurized breathable gas to be provided to a patient for treatment;
a pulse oximeter configured to non-invasively measure pulse oximetry of the patient and generate a pulse oximeter signal;
an airflow measurement patient interface configured to measure cardiogenic respiratory flow of the patient and generate a cardiogenic respiratory flow signal; and
a processor configured to:
determine or derive a patient respiratory effort signal from the pulse oximeter signal, the patient respiratory effort signal being indicative of a measure of patient respiratory effort associated with inspiring air into the lungs during a treatment period, calculate a pulse-transit time based at least in part on the cardiogenic respiratory flow signal and the pulse oximeter signal, and provide the pulse-transit time and/or the patient respiratory effort signal to the controllable flow generator as an input for controlling operation of the controllable flow generator.

26. The air delivery system of claim 25, wherein the processor is configured to at least one of discriminate between open-closed apnea, determine high airway resistance, determine relative work of breathing, augment control algorithms for the flow generator, determine overventilation, and determine sleep state, based on the patient respiratory effort signal.

27. The air delivery system of claim 25, wherein the processor is configured to distinguish between open and closed airway apneas based on the patient respiratory effort signal and the cardiogenic respiratory flow signal.

28. The air delivery system of claim 25, wherein the processor is configured to instruct the controllable flow generator to reduce pressure support when the measure of patient respiratory effort increases, and the processor is configured to instruct the controllable flow generator to increase pressure support when the measure of patient respiratory effort decreases.

29. The air delivery system of claim 25, wherein the pulse-transit time is calculated based on a delay between the cardiogenic respiratory flow signal and the pulse oximeter signal.

30. A method for treating sleep disordered breathing, comprising:

generating a supply of pressurized breathable gas to a patient with a flow generator for treatment of sleep disordered breathing;

receiving a pulse oximetry signal from a pulse oximeter;

determining or deriving a patient respiratory effort signal from the pulse oximetry signal with a processor, the patient respiratory effort signal being indicative of a measure of patient respiratory effort associated with inspiring air into the lungs during a treatment period;

receiving a cardiogenic respiratory flow signal from an airflow measurement patient interface;

calculating a pulse-transit time with the processor based at least in part on the cardiogenic respiratory flow signal and the pulse oximetry signal; and controlling the supply of pressurized breathable gas generated by the flow generator based on at least the pulse-transit time and/or the patient respiratory effort signal from the processor.

31. The method of claim 30, further comprising at least one of discriminating between open-closed apnea, determining high airway resistance, determining relative work of breathing, augmenting control algorithms for the flow generator, determining overventilation, and determining sleep state with the processor, based on the patient respiratory effort signal.

32. The method of claim 30, further comprising distinguishing between open and closed airway apneas with the processor based on the patient respiratory effort signal and the cardiogenic respiratory flow signal.

33. The method of claim 30, further comprising instructing the flow generator to reduce pressure support with the processor when the measure of patient respiratory effort increases, and instructing the flow generator to increase pressure support with the processor when the measure of patient respiratory effort decreases.

34. The method of claim 30, further comprising:

determining whether there is a long-term reduction in stroke volume for a period of time greater than a first predetermined period of time;

determining whether there is a long-term increase in respiratory baseline variation of the pulse oximetry signal for a period of time greater than a second predetermined period of time; and determining whether there is a long-term increase in the pulse-transit time for a period of time greater than a third predetermined period of time, wherein:

if there is a long-term reduction in stroke volume and no long-term increase in respiratory baseline variation of the pulse oximetry signal, then the method comprises generating an alert regarding and/or reporting elevated Sympathetic Nervous System output;

if there is no long-term reduction in stroke volume but there is a long-term increase in respiratory baseline variation of the pulse oximetry signal, then the method comprises generating an alert regarding and/or reporting cardiac decompensation; and if there is no long-term reduction in stroke volume and no long-term increase in respiratory baseline variation of the pulse oximetry signal, but there is a long term increase in the pulse-transit time, then the method comprises generating an alert regarding and/or reporting elevated Sympathetic Nervous System output.

35. The method of claim 30, wherein the pulse-transit time is calculated based on a delay between the cardiogenic respiratory flow signal and the pulse oximetry signal.

36. A respiratory effort monitoring apparatus, comprising:

a pulse oximeter configured to non-invasively measure pulse oximetry of a patient and generate a pulse oximeter signal;

a processor configured to receive the pulse oximeter signal and generate a patient respiratory effort signal that is indicative of respiratory rate and of patient respiratory effort associated with inspiring air into the lungs;

an airflow measurement device configured to measure cardiogenic respiratory flow of the patient and generate a cardiogenic respiratory flow signal; and a processor configured to calculate relative variations in pulse-transit time based at least in part on the cardiogenic respiratory flow signal and the pulse oximeter signal.

37. The apparatus of claim 36, wherein the patient respiratory effort signal and/or variations in pulse-transit time are used as inputs to control operation of a controllable flow generator operable to generate a supply of pressurized breathable gas to be provided to a patient for treatment.

38. A method for treating sleep disordered breathing, comprising:

non-invasively measuring pulse oximetry of a patient and deriving a pulse oximeter signal from the pulse oximetry measured with a pulse oximeter;

measuring cardiogenic flow of the patient and deriving a cardiogenic flow signal from the cardiogenic flow measured with an airflow measurement device;

calculating a pulse-transit time based on the pulse oximeter signal and the cardiogenic flow signal with a processor; and generating a patient respiratory effort signal based on the pulse-transit time, wherein the patient respiratory effort signal is indicative of respiratory rate and patient respiratory effort that is associated with inspiring air into the lungs.

39. The method of claim 38, further comprising controlling a supply of pressurized breathable gas to a patient for treatment based on input from the patient respiratory effort signal.

40. The method of claim 38, wherein the pulse-transit time is calculated based on a delay between the cardiogenic flow signal and the pulse oximeter signal.

41. A method of monitoring a patient parameter, the method comprising:
    non-invasively monitoring pulse oximeter plethysmography of a patient with a pulse oximeter;
    generating a patient respiratory effort signal from said pulse oximeter plethysmography with a processor;
    determining a measure of patient respiratory effort from the patient respiratory effort signal with the processor;
    measuring cardiogenic respiratory flow and generating a cardiogenic respiratory flow signal with an airflow measurement device; and
    controlling a flow generator based on the patient respiratory effort signal and the cardiogenic respiratory flow signal,
    wherein the patient respiratory effort signal is generated from said pulse oximeter plethysmography based on at least one of variations in a peak-to-peak amplitude of an arterial blood pressure waveform of the pulse oximeter plethysmography, a pulse rhythm of the arterial blood pressure waveform, and a baseline of the arterial blood pressure waveform.

42. The method of claim 41, further comprising non-invasively monitoring the pulse oximeter plethysmography with the pulse oximeter while the patient is sleeping.

43. The method of claim 41, wherein said patient respiratory effort signal is indicative of the extent to which the patient is suffering from sleep disordered breathing.

44. The method of claim 43, wherein said patient respiratory effort signal is indicative of upper airway obstruction.

45. A method for delivering positive pressure therapy by a servo-ventilator to a patient having a health disorder, comprising:
    non-invasively measuring pulse oximetry of the patient and generating a pulse oximeter signal with a pulse oximeter;
    deriving a measure of patient respiratory effort associated with inspiring air into the lungs from the pulse oximeter signal with a processor;
    measuring cardiogenic respiratory flow of the patient and generating a cardiogenic respiratory flow signal with an airflow measurement interface;
    calculating a pulse-transit time (PTT) with the processor based at least in part on the cardiogenic respiratory flow signal and the pulse oximeter signal; and
    controlling variables in the servo-ventilator based on the measure of patient respiratory effort and/or the calculated PTT;
    wherein when the measure of patient respiratory effort increases, the servo-ventilator is configured to reduce pressure support, and
    wherein when the measure of patient respiratory effort decreases, the servo-ventilator is configured to increase pressure support.

46. The method of claim 45, wherein the health disorder is sleep disordered breathing, congestive heart failure, or stroke.

47. The method of claim 45, wherein the pulse-transit time is calculated based on a delay between the cardiogenic respiratory flow signal and the pulse oximeter signal.

48. A method for delivering positive pressure therapy by a CPAP ventilator to a patient having a health disorder, the method comprising
    non-invasively measuring pulse oximetry of the patient and generating a pulse oximetry signal with a pulse oximeter;
    generating a patient respiratory effort signal indicative of patient respiratory effort exerted by the patient in dependence on the pulse oximetry signal generated by the pulse oximeter with a processor;
    measuring a cardiogenic respiratory flow of the patient and generating a cardiogenic respiratory flow signal with an airflow measurement device;
    calculating relative variations in pulse-transit time with the processor based at least in part on the cardiogenic respiratory flow signal and the pulse oximetry signal; and
    inputting the relative variations in pulse-transit time from the processor to a feedback controller of the ventilator to control positive pressure therapy to the patient.

* * * * *